(12) United States Patent
Jain et al.

(10) Patent No.: US 6,740,080 B2
(45) Date of Patent: May 25, 2004

(54) ABLATION SYSTEM WITH SELECTABLE CURRENT PATH MEANS

(75) Inventors: Mudit K. Jain, Woodbury, MN (US); Milton M. Morris, Minneapolis, MN (US); Bruce KenKnight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 85 days.

(21) Appl. No.: 09/945,097

(22) Filed: Aug. 31, 2001

(65) Prior Publication Data

US 2003/0045871 A1 Mar. 6, 2003

(51) Int. Cl.[7] ............................................... A61B 18/12
(52) U.S. Cl. ......................................... 606/34; 606/41
(58) Field of Search ..................... 606/32–50

(56) References Cited

U.S. PATENT DOCUMENTS

| | | | |
|---|---|---|---|
| 5,683,384 A | * | 11/1997 | Gough et al. .................. 606/41 |
| 5,693,078 A | * | 12/1997 | Desai et al. ................. 607/102 |
| 5,766,165 A | | 6/1998 | Gentelia et al. |
| 5,957,961 A | * | 9/1999 | Maguire et al. ............... 607/99 |
| 6,283,987 B1 | * | 9/2001 | Laird et al. .................... 607/96 |
| 6,319,249 B1 | * | 11/2001 | Tollner ......................... 606/34 |
| 6,337,998 B1 | * | 1/2002 | Behl et al. .................. 607/101 |
| 6,391,024 B1 | * | 5/2002 | Sun et al. ...................... 606/34 |

* cited by examiner

Primary Examiner—Roy D. Gibson
Assistant Examiner—Aaron Roane
(74) Attorney, Agent, or Firm—Fulwider Patton Lee & Utecht, LLP (57) ABSTRACT

An apparatus for delivering energy to a biological site includes a catheter having an ablation electrode and a plurality of backplates distributed at various locations proximal the biological site. The backplates are coupled to a switching device for selecting which backplate to utilize as a return electrode to complete the circuit with the ablation electrode in order to obtain deeper, larger lesions for a given amount of energy. The backplate selection is made by determining which return electrode most closely places the biological site between the ablation electrode and the backplate. Backplate selection may be made automatically based on impedance measurements or conduction time measurements. Alternatively, the backplate selection can be made manually.

27 Claims, 5 Drawing Sheets

ABLATION SYSTEM WITH SELECTABLE CURRENT PATH MEANS

BACKGROUND OF THE INVENTION

1. Field of the Invention

The invention relates generally to an electrophysiological ("EP") system for providing radio frequency ("RF") energy to biological tissue and, more particularly, to an ablation system having multiple selectable current path means for directing the flow of current through tissue in energy and time efficient manners.

2. Description of Related Art

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system.

There are two general methods of applying RF energy to cardiac tissue, unipolar and bipolar. In the unipolar method a large surface area electrode; e.g., a backplate, is typically placed on the back of the patient to serve as a return. The backplate completes an electrical circuit with one or more electrodes that are introduced into the heart, usually via a catheter, and placed in intimate contact with the aberrant conductive tissue. In the bipolar method, electrodes introduced into the heart have different potentials and complete an electrical circuit between themselves. In the bipolar method, the flux traveling between the two electrodes of the catheter enters the tissue to cause ablation.

During ablation, electrodes carried by an EP catheter are placed in intimate contact with the target endocardial tissue. RF energy is applied to the electrodes to raise the temperature of the target tissue to a non-viable state. In general, the temperature boundary between viable and non-viable tissue is approximately 48° Centigrade. Tissue heated to a temperature above 48° C. becomes non-viable and defines the ablation volume. The objective is to elevate the tissue temperature, which is generally at 37° C., fairly uniformly to an ablation temperature above 48° C., while keeping both the temperature at the tissue surface and the temperature of the electrode below 100° C. When the blood temperature reaches approximately 100° C., coagulum can occur. Blood coagulation is a major limitation or complication associated with RF ablation therapy. Coagulation can lead to thromboembolism and also form an insulating layer around the electrode, thereby hindering further energy delivery required for ablation therapy. Thus, heating of blood is a major concern for ablation safety and efficacy.

Figure 1:
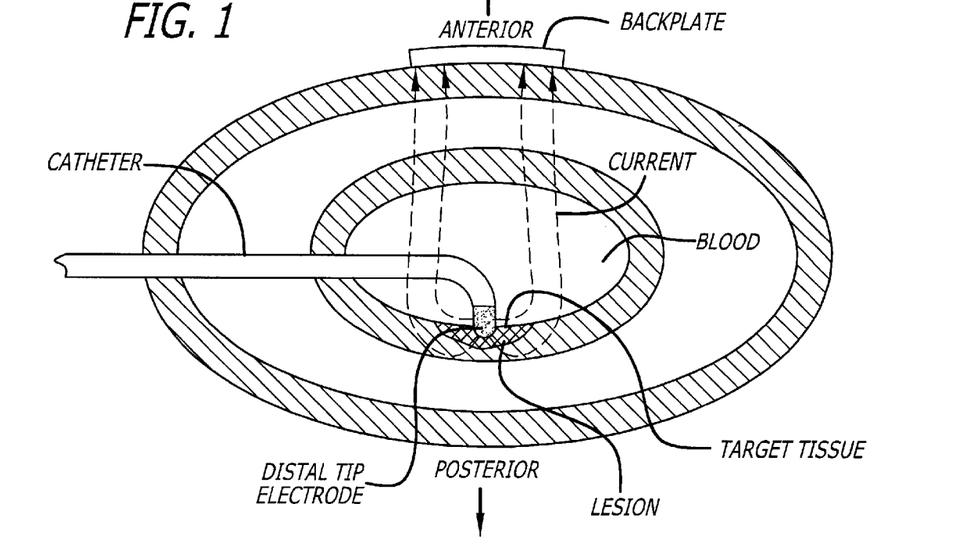
FIG. 1 is a cross section depicting an ablation catheter within a biological site that is within a biological body and the current flow from the catheter to a return electrode.

A basic configuration of an RF ablation system, as shown in FIG. 1, includes an ablation catheter and a backplate. The ablation catheter includes a distal tip which is fitted with a tip electrode for applying RF energy. The tip electrode is the source of an electrical signal that causes heating of the contacting and neighboring tissue. The tip electrode act as one electrical pole. The other electrical pole is provided by the backplate which is in contact with a patient's external body part. The backplate acts as a current path means in that it establishes a current path with respect to the tip electrode. During operation, a RF signal, typically in the 500 kHz region, is applied to the tip electrode. The current path for the RF signal established between the tip electrode and the backplate produces a localized RF heating effect in the tissue which in turn produces a lesion. In order to obtain a deep, localized lesion at the contacting tissue, i.e., target tissue, using a given amount of RF energy, the backplate and tip electrode should be optimally positioned relative each other, not as shown in FIG. 1, such that the target tissue is located between the tip electrode and the backplate. However, the backplate may not always be located in the optimal position. Specifically, if the backplate is positioned such that the target tissue is not between the ablating tip electrode and the backplate, as shown in FIG. 1, the current that enters the tissue conducts away from the tissue interior toward the backplate, causing more energy to be dissipated into the blood. The net result of the redistribution of current is a measurable difference in lesion depth and size. In order to obtain a lesion of quality similar to that obtainable when the backplate is in the optimal position, the amount of current flowing through the tissue must be increased. However, this presents a risk that the blood may be heated to the point where coagulum forms (100° C.) before achieving a desired lesion volume. Alternatively, the backplate may be physically repositioned on the patient in order to place it in the optimal position. This is undesirable for the patient because it increases the overall time of the procedure.

Hence, those skilled in the art have recognized a need for an ablation system having multiple and selectable current path means for directing a current through target tissue to thereby create a quality lesion in a safe and efficient manner. The invention fulfills these needs and others.

SUMMARY OF THE INVENTION

Briefly, and in general terms, the invention is directed to a system and method for selectively providing RF energy to biological tissue and, more particularly, to an ablation system having multiple selectable current path means for directing the flow of current through tissue in energy and time efficient manners.

In one aspect, the invention relates to a system for delivering energy to any one of a plurality of tissue regions at a biological site within a biological body. The system includes at least one primary electrode that is adapted to be positioned adjacent any one of the plurality of tissue regions. Also included in the system is a plurality of secondary electrodes adapted to be positioned about the biological site such that any one of the plurality of tissue regions is interposed between at least one of the secondary electrodes and the at least one primary electrode. The system also includes a power generator that is adapted to provide power to the at least one primary electrode. Further included is a switching device that is adapted to selectively couple one of the secondary electrodes to an electrical device. The electrical device is adapted to maintain the selected secondary electrode at a voltage level that is different from the primary electrode such that current flows from the primary electrode through the tissue region to the selected secondary electrode.

In a detailed aspect, the at least one primary electrode within the system is disposed at a distal segment of a first catheter. The first catheter is adapted to be positioned within the biological body. In a further aspect, at least one of the secondary electrodes includes a backplate that is adapted to be positioned adjacent the exterior of the biological body. In another aspect, at least one of the secondary electrodes is disposed at a distal segment of a second catheter that is also adapted to be positioned within the biological body. In an additional aspect, the primary electrode and at least one of the secondary electrodes are disposed at a distal segment of a single catheter that is adapted to be positioned within the biological body.

In an additional facet, the system includes a controller that is adapted to select one of the secondary electrodes for coupling with the electrical device and to command the switching device to couple the selected secondary electrode to the electrical device. In one detailed facet, the controller is adapted to measure the impedance between each of the secondary electrodes and the primary electrode, compare the impedances and based on the comparison, select the secondary electrode for coupling to the electrical device. In a further detailed facet, in order to measure the impedance between each of the secondary electrodes and the primary electrode, the controller is adapted to apply an electric pulse at the primary electrode, sense the electric pulse at a first of the secondary electrodes, calculate the difference between the voltage of the pulse signal and the voltage of the sensed signal to determine the impedance, and repeat the process for each of the remaining secondary electrodes. In another detailed aspect, the controller is adapted to measure the conduction time of a pulse between each of the secondary electrodes and the primary electrode, compare the conduction times and based on the comparison, select the secondary electrode for coupling to the electrical device. In a further detailed aspect, the secondary electrode with the shortest conduction time is selected.

In a second aspect, the invention relates to a system for providing a plurality of selectable current paths through a plurality of tissue regions within a biological site within a biological body. The system includes at least one primary electrode that is adapted to be positioned adjacent any one of the plurality of tissue regions and to serve as a first electrical pole. The system also includes a plurality of secondary electrodes adapted to be positioned about the biological site such that any one of the plurality of tissue regions is interposed between at least one of the secondary electrodes and the primary electrode. Each of the secondary electrodes is adapted to be selected to serve as a second electrical pole having a voltage different than the first electrical pole such that current flows through the tissue region between the first and second electrical poles. Further included in the system is a selection system adapted to select one of the secondary electrodes as the second electrical pole.

In a detailed aspect, the selection system includes a switching device that is adapted to selectively couple one of the secondary electrodes to an electrical device. The electrical device is adapted to maintain the selected secondary electrode at a voltage level different than the primary electrode. In a further aspect, the selection system includes a controller that is adapted to select one of the secondary electrodes for coupling with the electrical device and to command the switching device to couple the selected secondary electrode to the electrical device. In a detailed aspect, the controller is adapted to measure the impedance between each of the secondary electrodes and the primary electrode, compare the impedances and based on the comparison, select the secondary electrode for coupling to the electrical device. In another detailed aspect, the controller is adapted to measure the conduction time of a pulse between each of the secondary electrodes and the primary electrode, compare the conduction times and based on the comparison, select the secondary electrode for coupling to the electrical device.

In a third aspect, the invention relates to a method for selectively ablating any one of a plurality of tissue regions within a biological site of a biological body. The method includes positioning at least one primary electrode adjacent one of the plurality of tissue regions. The method also includes positioning a plurality of secondary electrodes about the biological site. The method further includes selecting which of the plurality of secondary electrodes is positioned such that the tissue region adjacent the at least one primary electrode is interposed between the primary electrode and the secondary electrode. Additionally, the method includes providing energy to the primary electrode and maintaining the selected secondary electrode at a voltage level different from the primary electrode such that current flows from the primary electrode through the tissue region to the selected secondary electrode.

In a detailed aspect, positioning the plurality of secondary electrodes about the biological site includes positioning at least one secondary electrode adjacent the biological body at each of the anterior, posterior, lateral, and septal positions on the biological body. In another aspect, positioning the plurality of secondary electrodes about the biological site includes positioning the secondary electrodes adjacent the biological body in several locations about the outer surface of the biological body. In a further aspect, positioning the plurality of secondary electrodes about the biological site encompasses positioning at least one of the secondary electrodes within the biological body and about the biological site such that the tissue region is interposed between the primary electrode and the secondary electrode. In an additional aspect, positioning the plurality of secondary electrodes about the biological site includes positioning a plurality of secondary electrodes within the biological body and about the biological site. In a detailed facet of the invention, selecting the secondary electrode includes measuring the impedance between each of the secondary electrodes and the primary electrode, comparing the impedance between each of the secondary electrodes and the primary electrode, and selecting the secondary electrode with the lowest impedance. In a more detailed facet, measuring the impedance between each of the secondary electrodes and the primary electrode includes applying an electric pulse at the primary electrode, sensing the electric pulse at a first of the secondary electrodes, calculating the difference between the voltage of the pulse signal and the voltage of the sensed signal to determine the impedance, and repeating these steps for each of the remaining secondary electrodes.

These and other aspects and advantages of the invention will become apparent from the following detailed description and the accompanying drawings which illustrate by way of example the features of the invention.

DETAILED DESCRIPTION OF THE PREFERRED EMBODIMENTS

Figure 2:
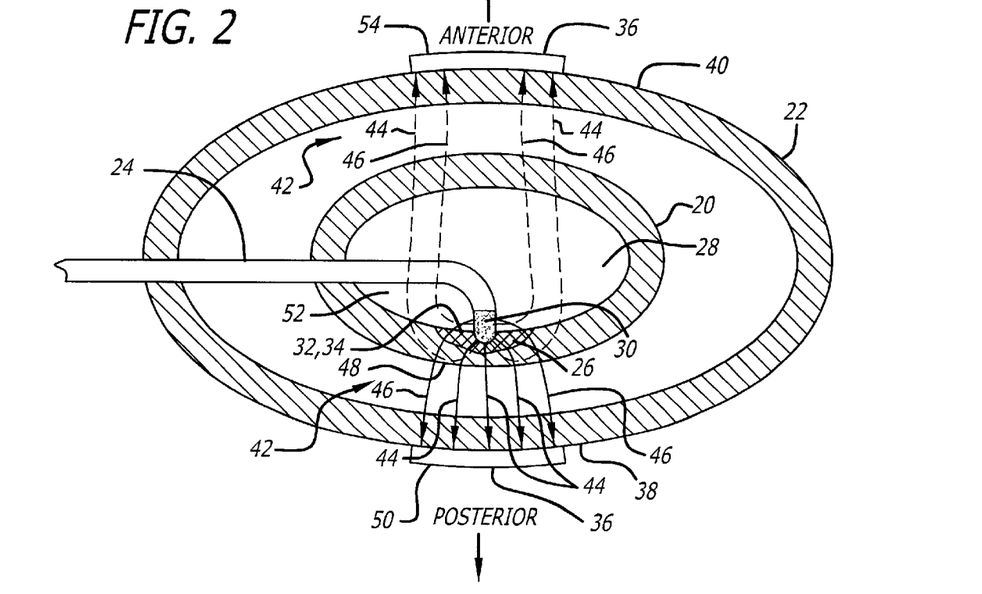
FIG. 2 is a cross section depicting an ablation catheter within a biological site that is within a biological body and the current flow from the catheter to return electrodes.

Referring now to the drawings, wherein the reference numerals denote like or corresponding parts throughout the figures, in FIG. 2 there is shown a biological site 20 within a biological body 22. An ablation catheter 24 for producing a lesion 26 at any one of a plurality of tissue regions is depicted within a cavity 28 of the biological site 20, with a primary electrode 30 or ablation electrode at the distal tip of the catheter. The primary electrode 30 is positioned adjacent a posterior surface region 32 of the biological tissue 34 defining the biological site 20. The lesion 26 is produced by delivering energy through the primary electrode 30 to the biological tissue 34. A secondary electrode 36 or backplate is shown adjacent a posterior surface 38 of the biological body 22, which places the backplate in front of or opposite the distal tip electrode 30. A second backplate 36 is shown adjacent an anterior surface 40 of the biological body. The secondary electrodes 36 function as current path means in that they serve to complete an electrical circuit with the primary electrode 30 of the catheter 24.

The optimal and most energy efficient position for the backplate 36 for obtaining deeper and larger lesions is in front of, or opposite, the tip electrode 30 or primary electrode, wherein the tissue region 34 being ablated is located between the ablating tip electrode and the backplate or secondary electrode. There are two effects of moving the backplate 36 from the optimal position opposite the primary electrode 30 to the least optimal and most energy inefficient position behind the primary electrode for ablation. The first and most significant effect is on joule heating efficiency. Less energy is required per unit volume of lesion for the optimal backplate 36 position than for a non-optimal position, a result of the distribution of the current leaving the primary electrode 30 of the catheter 24. The second effect is the difference in lesion size for a given level of energy that can be attributed to a change in the current flow pattern under the primary electrode 30.

The current 42 leaving the tip electrode 30 or primary electrode has two components: the tissue current 44 and the blood current 46. With the configuration depicted in FIG. 2, the optimal position for the backplate 36 is adjacent the posterior surface 38 of the biological body 22. The current 42 flowing to the backplate 36 in the optimal position is depicted in solid lines. With the backplate 36 adjacent the posterior surface 38 of the biological body 22, the tissue current 44 leaves the primary electrode 30 and enters the tissue 34 directly. The tissue current 44 then passes through the lesion volume 26, out through the outer surface 48 of the tissue 34, and then through the biological body 22 to the posterior backplate 50 that is located adjacent the posterior surface of the biological body. The joule heating of the tissue 34 immediately adjacent to the primary electrode 30 is caused by the tissue current 44. The tissue current 44 is the primary determinant of the primary electrode 30 temperature. When the backplate 36 is placed in front of the primary ablation electrode 30, a very high percentage of the total current 42 enters the tissue 34 and is used to maintain the temperature of the primary electrode. With a high percentage of the current 42 entering the tissue 34, less current is available to heat the blood pool 52, hence, undesirable heating of the blood is reduced. The blood current 46, on the other hand, enters the blood pool 52 directly, a result of a portion of the primary electrode 30 being located within a blood pool within the cavity 28 of the biological site 20. The blood current 46 passes through the blood pool 52, into the tissue 34, out through the outer surface 48 of the tissue 34, and then through the biological body 22 to the posterior backplate 50 that is adjacent the posterior surface of the biological body. Although the bulk of the lesion 26 is formed by heat conducted outward from the primary electrode 30, the tissue current 44 and blood current 46 passing through the lesion space adds marginally to the lesion volume by increasing the joule heating within the lesion.

With further reference to FIG. 2, with the tip electrode 30 or primary electrode disposed at the posterior surface region 32 of the biological site cavity 28 and the anterior backplate 54 serving as the secondary electrode (the non-optimal position), the current 42 that enters the tissue 34 conducts toward the blood pool 52, causing more energy to be dissipated into the blood. The current 42 flowing to the backplate 36 in the non-optimal position is depicted in dashed lines. The net result of the redistribution of current is a measurable difference in lesion size (see FIG. 1). In order to maintain the tissue current 44, and hence a constant temperature, the total current 42 from the tip electrode 30 must increase. However, as previously mentioned, this presents a risk that the blood 52 may be heated to the point where coagulum forms (100° C.) before achieving a desired lesion volume 26.

As also previously mentioned, the other effect of moving the backplate 36 from the optimal position to the least optimal position is the size of the lesion produced, a result of changes in the current flow pattern under the primary electrode 30. Resistive heating of the tissue 34 during RF ablation is inversely proportional to approximately the fourth power of the distance from the primary electrode 30. This strong dependence on distance dominates the lesion formation process. Although changes in the backplate 36 location have a small effect on current densities very close to the primary electrode 30, as shown in FIG. 2 the current distribution, and hence lesion characteristics, does change when the backplate is positioned in front of, instead of behind, the primary electrode.

Figure 3:
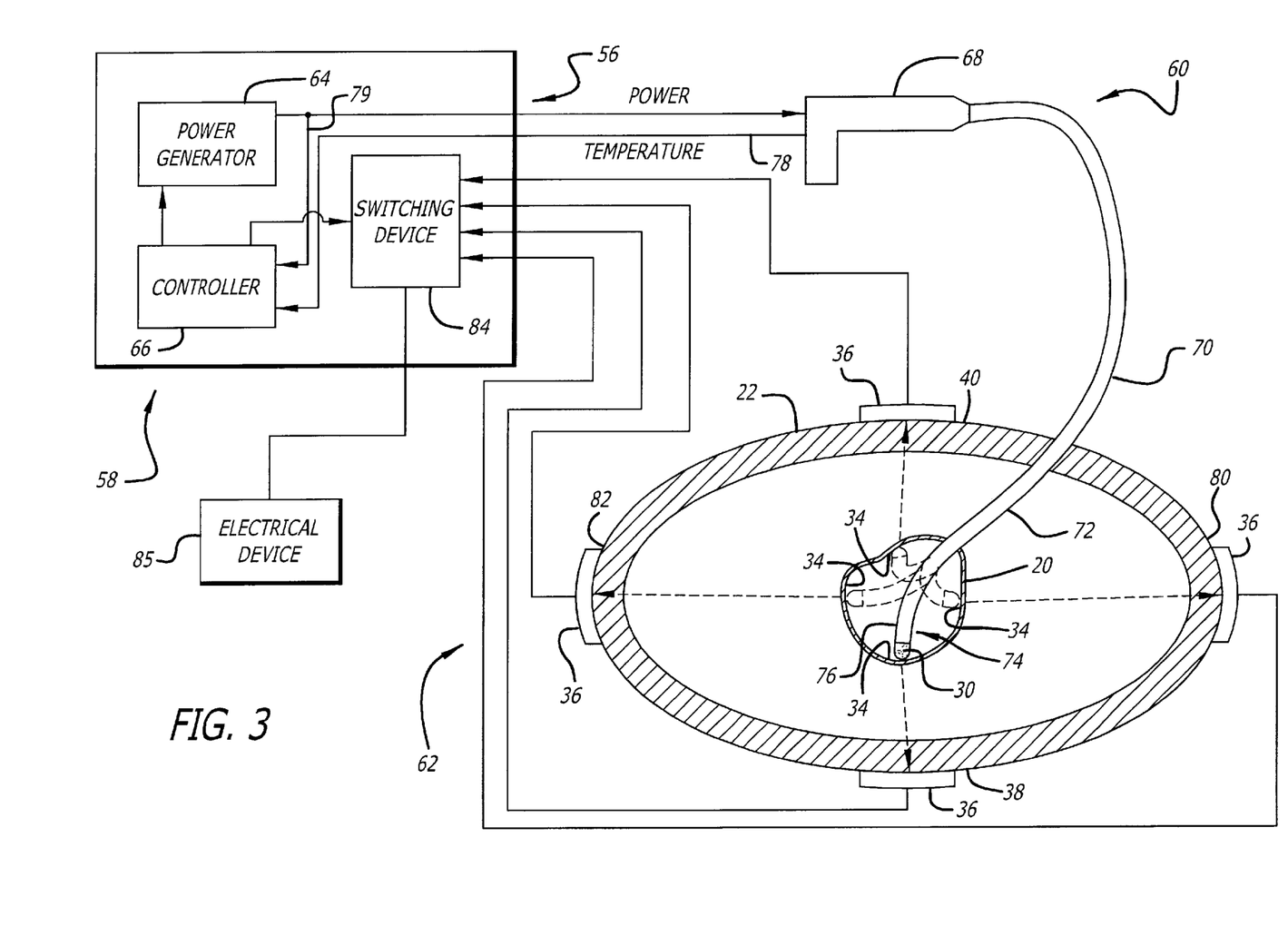
FIG. 3 is a schematic of an ablation system for ablating the biological site.

Based on the foregoing, in FIG. 3 there is shown an ablation system 56 configured in accordance with the present invention for ablating biological tissue 20, e.g. the atrium or ventricle of the heart, that utilizes multiple current path means, i.e., backplates 36 or secondary electrodes in order to create deeper, larger lesions while decreasing blood heating, as compared to prior art ablation systems. The system includes a power control system 58, a catheter system 60, and a secondary electrode system 62. The power control system 58 includes an electrical source, such as a power generator 64, that may have any number of output channels through which it provides power to the catheter system 60. In one embodiment, the power generator 64 provides RF energy. The operation of the power generator 64 is controlled by a controller 66 that outputs control signals to the power generator. The controller 66 monitors and adjusts the power provided by the power generator 64. The configuration and operation of the controller 66 and power generator 64 are similar to the controller and power generator disclosed in U.S. Pat. No. 6,059,778, entitled "RF Ablation Apparatus and Method Using Unipolar and Bipolar Techniques," the disclosure of which is hereby incorporated by reference.

With continued reference to FIG. 3, the catheter system 60 includes a handle 68 and a sheath 70 having a distal segment 72. The distal segment 72 includes an ablation electrode system 74 and is capable of being percutaneously introduced into a biological site 20 and positioned adjacent any one of a plurality of tissue regions 34 within the biological site 20. In one embodiment, the ablation electrode system 74 includes a tip primary electrode 30 at the distal end 76 of the catheter 60. In use, the primary electrode 30 is placed adjacent the target biological tissue region 34 at the location that is to be ablated. The primary electrode 30 is formed of a material having a significantly higher thermal conductivity than that of the biological tissue to be ablated. Possible materials include silver, gold, chromium, aluminum, molybdenum, tungsten, nickel, platinum, and platinum/10% iridium. Although only a tip ablation electrode 30 is depicted, the ablation electrode system may also include one or more band electrodes (not shown).

Associated with the ablation electrode system 74 are thermal sensors (not shown) for monitoring the temperature of the electrode system. The thermal sensors are mounted to the tip primary electrode 30, or to each electrode in a multiple ablation electrode system. Each thermal sensor provides a temperature signal 78 to the controller 66 which is indicative of the temperature of the respective primary electrode at that sensor. Based on the temperature signals 78 that the controller 66 receives from the ablation electrode system 74, as well as power signals 79 received from the power generator 64, the controller adjusts the operation of the power generator to maintain the temperature of the primary electrodes 30 within a desired range to obtain a deep and large lesion without heating the surrounding blood 52 to such level that coagulum forms.

With further reference to FIG. 3, the secondary electrode system 62 includes a plurality of backplates 36 or secondary electrodes which function as current path means. The backplates 36 are positioned at various locations adjacent the biological body 22 and about the biological site 20. In one embodiment, the secondary electrode system 62 includes four backplates 36 distributed so that one each is adjacent an anterior 40, lateral 80, septal 82, and posterior 38 position on the surface of the biological body 22. In another embodiment, the secondary electrode system 62 includes more than four backplates 36 (not shown). The extra backplates 36 can be positioned anywhere adjacent the surface of the biological body 22.

The backplates 36 or secondary electrodes are connected to a switching device 84 that is adapted to selectively couple one of the secondary electrodes to an electrical device 85. The secondary electrode 36 is selected so that the target tissue region 34 lies between the primary electrode 30 and the selected backplate or secondary electrode 36 The electrical device 85 is adapted to maintain the selected secondary electrode 36 at a voltage level that is different from the voltage level of the primary electrode 30, thereby permitting current to flow between the primary electrode and the secondary electrode. For example, in one embodiment, the electrical device 85 maintains the potential of the secondary electrode 36 at zero volts. In another embodiment the electrical device 85 is ground. In a further embodiment, the electrical device 85 provides an AC signal having a voltage lower than that of the power signal 79 provided to the primary electrode 30 by the power generator 64. Although the electrical device 85 is depicted as a separate component of the ablation system 56, the electrical device may be incorporated in the power control system 58.

Before selecting which secondary electrode 36 to couple to the electrical device 85, the location of the primary electrode 30 on the biological tissue 34 to be ablated is determined. Then the switching device 84 is utilized to select which backplate 36 will be used as the secondary electrode; i.e. the backplate that most closely places the biological target tissue 34, or tissue region, between the primary electrode 30 and the backplate 36. In one embodiment, the operator manually selects which backplate 36 to use, while in another embodiment, the backplate selection is performed automatically.

During manual selection, the operator uses a means such as fluoroscopy, to determine the location of the primary ablation electrode 30 relative to the surface of a tissue region 34 and the secondary electrode 36. The operator then determines which secondary electrode 36 or backplate places the tissue region 34 most closely between the primary electrode 30 and the backplate. The operator then selects that backplate with the switching device 84 to be the secondary electrode for the ablation procedure. In one embodiment the switching device 84 is a mechanical device, such as a rotary switch. In another embodiment the switching device 84 is a software implemented switch activated by keyboard or touchscreen entry.

During automatic selection the controller 66 is used to determine which secondary electrode 36 or backplate is in the optimal position. During the secondary electrode 36 selection process, the controller 66 commands the power generator 64 to output a low energy pulse signal to the ablation electrode 30. The characteristics of the pulse signal, e.g., the voltage, timing and width, are selected such that the pulse is not pro-arrthymic, i.e., it does not induce cardiac arrthymia. The controller 66 also commands a switching device 84, such as a multiplexer, to connect a first secondary electrode 36 of the plurality of secondary electrodes to the switching device output that interfaces with the controller. Through this interface, the controller 66 senses the receipt of the pulse signal at the connected secondary electrode 36. Using the voltage and current of the pulse signal and the voltage of the sensed signal, the controller 66 calculates the impedance between the ablation electrode and the selected secondary electrode. Once the first measurement is obtained, the controller 66 commands the switching device 84 to connect another of the plurality of the secondary electrodes 36 to the switching device output which interfaces with the controller. The controller 66 then commands the power generator 64 to output another pulse and the impedance between the ablation electrode 30 and the second of the secondary electrodes 36 is determined. This process is repeated for each of the secondary electrodes 36. Impedance measurements are affected by the location of the backplate. More specifically, the greater a distance for the pulse to travel generally equates to a higher impedance measurement. However, the consistency of the matter through which the pulse travels can also affect impedance. For example, blood provides less resistance, and thus lower impedance measurements, than muscle. Once all impedance measurements are obtained, the controller 66 compares the measurements and selects the secondary electrode having the lowest impedance measurement as the optimal secondary electrode 36. The controller then commands the switching device 84 to connect the optimal secondary electrode 36 to the electrical device 85, and the ablation procedure may then begin.

An alternative method of selecting which secondary electrode 36 is in the optimal position involves conduction time measurement. Using this method, the controller commands the power generator 64 to output a low energy, non pro-arrhythmic pulse to the ablation electrode 30. The controller 66 also commands the switching device 84 to connect a first secondary electrode 36 of the plurality of secondary electrodes to the switching device output that interfaces with the controller. Through this interface, the controller 66 senses the receipt of the pulse signal at the connected secondary electrode 36 and measures the time between the sending of the pulse and the receipt of the pulse by the secondary electrode. This process is repeated for each of the secondary electrodes 36. Once all conduction time measurements are obtained, the controller 66 compares the measurements and selects the secondary electrode having the shortest conduction time measurement as the optimal secondary electrode 36. The controller 66 then commands the switching device 84 to connect the optimal secondary electrode 36 to the electrical device 85, and the ablation procedure may then begin.

Figure 4:
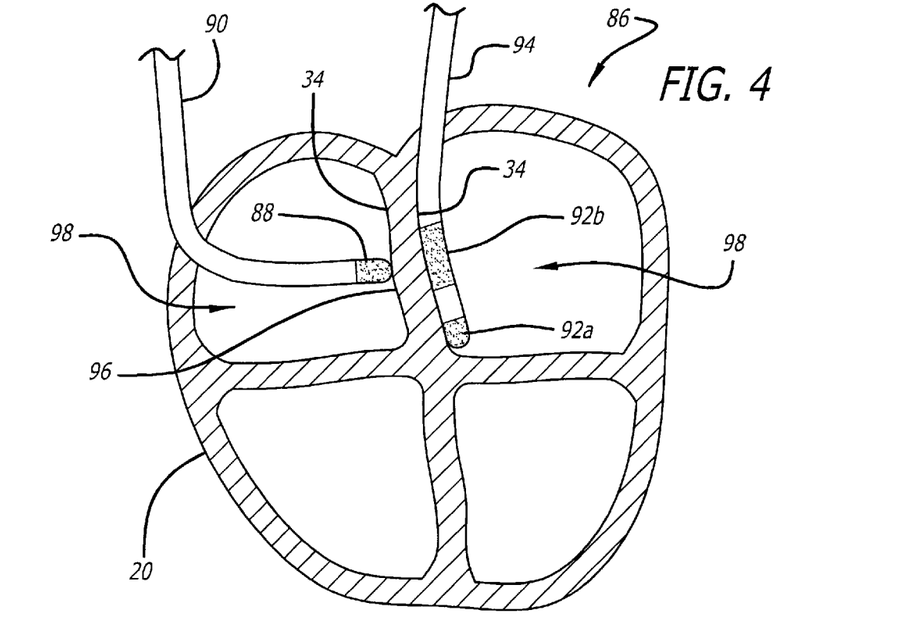
FIG. 4 is a cross section depicting an ablation catheter on one side of the biological site and a catheter with a return electrode on the opposite side of the biological site.
Figure 5:
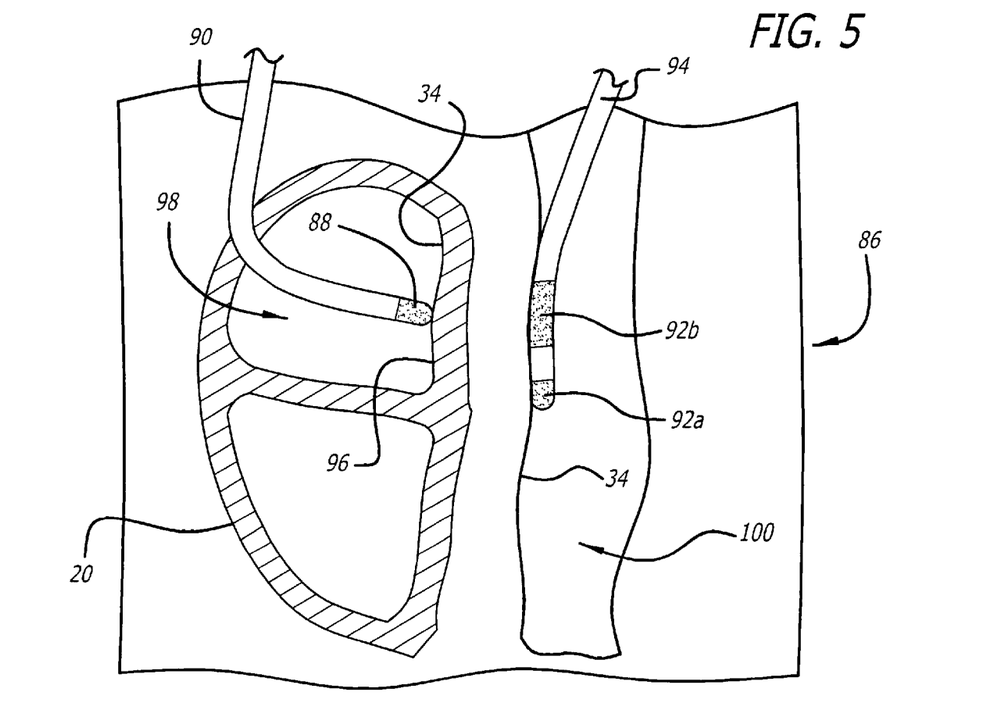
FIG. 5 is a cross section depicting an ablation catheter disposed at a biological site and a catheter with return electrodes within a corporeal vessel proximal the biological site.

With reference to FIGS. 4 and 5, another embodiment of the invention includes a catheter based secondary electrode system 86. In this embodiment, one or more ablation electrodes 88 or primary electrodes are distributed on a first catheter 90 while one or more secondary electrodes 92a, 92b are distributed on a second catheter 94. When multiple secondary electrodes are used, the secondary electrodes 92a, 92b are coupled to the switching device 84 (FIG. 3) to selectively couple one of the secondary electrodes to the electrical device 85 (FIG. 3). In use, the first catheter 90 is positioned at a tissue region 34 at the biological site 20 such that the ablation electrode 88 is placed adjacent the biological target tissue region 34, such as a surface 96 within a cardiac chamber 98. The second catheter 94 is also distributed at a tissue region 34 at the biological site 20, but in such manner that the selected secondary electrode 92a, 92b is positioned so that the target tissue region 34 lies between the ablation electrode 88 and the secondary electrode. For instance, when the target tissue region 34 is on a surface 96 within a cardiac chamber 98, possible locations for the secondary electrode 92a, 92b include other cardiac chambers 98 (FIG. 4), the esophagus 100 (FIG. 5), or a corporeal vessel (not shown). In another embodiment (not shown), the catheter based secondary electrode system 86 may interface with the switching device 84 (FIG. 3) and thereby be used in conjunction with the backplates 36 of the earlier discussed secondary electrode system 62 (FIG. 3) so that the operator or controller 66 can select a secondary electrode from either the backplates 36 or the secondary electrodes 92a, 92b on the second catheter 94. This embodiment provides a multitude of selectable current path means which enable the operator to further limit the area in which the energy travels within the biological body 22. Limiting the path of the energy reduces the likelihood of causing collateral damage to other tissue.

With further reference to FIG. 4, the configuration of the secondary electrode 92a, 92b can vary depending on the desired lesion 26. For instance, when the primary electrode 88 and the secondary electrode 92a, 92b are located on opposite sides of the target tissue region 34, a symmetric lesion can be created by having a secondary electrode 92a about the same size and density as the primary electrode. Similarly, a more diffuse lesion can be created by having a secondary electrode 92b that is larger than the primary electrode 88. As for the backplates 36 (FIG. 3), a more focused and deep lesion 26 can be created with a smaller backplate, while a larger backplate creates a larger, more diffuse lesion. The conductivity of the secondary electrode 36 or backplate also affects the lesion. More specifically, a secondary electrode 36 with higher conductivity produces a more focused, deeper lesion 26.

Figure 6:
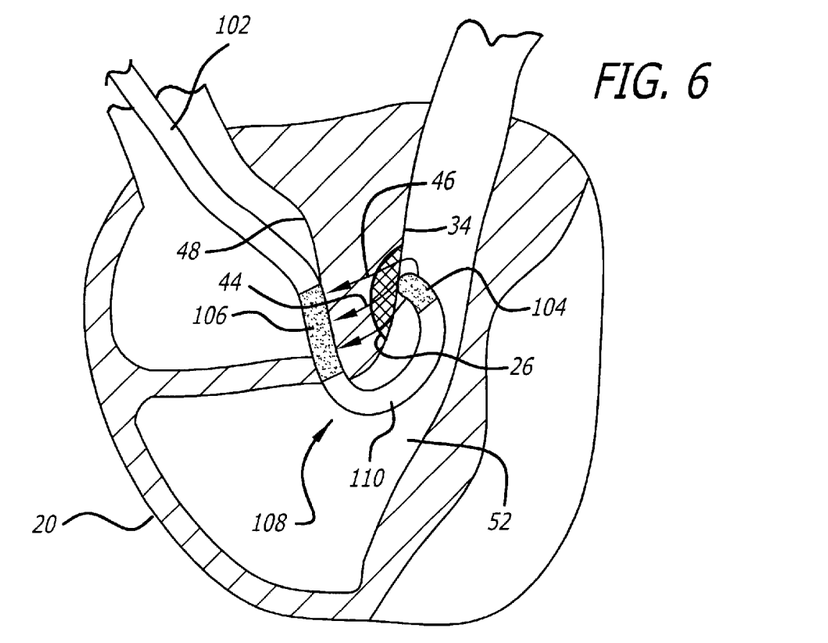
FIG. 6 is a cross section depicting a catheter with an ablation electrode disposed against a surface of the biological site and a return electrode disposed on the opposite surface of the biological site.
Figure 7:
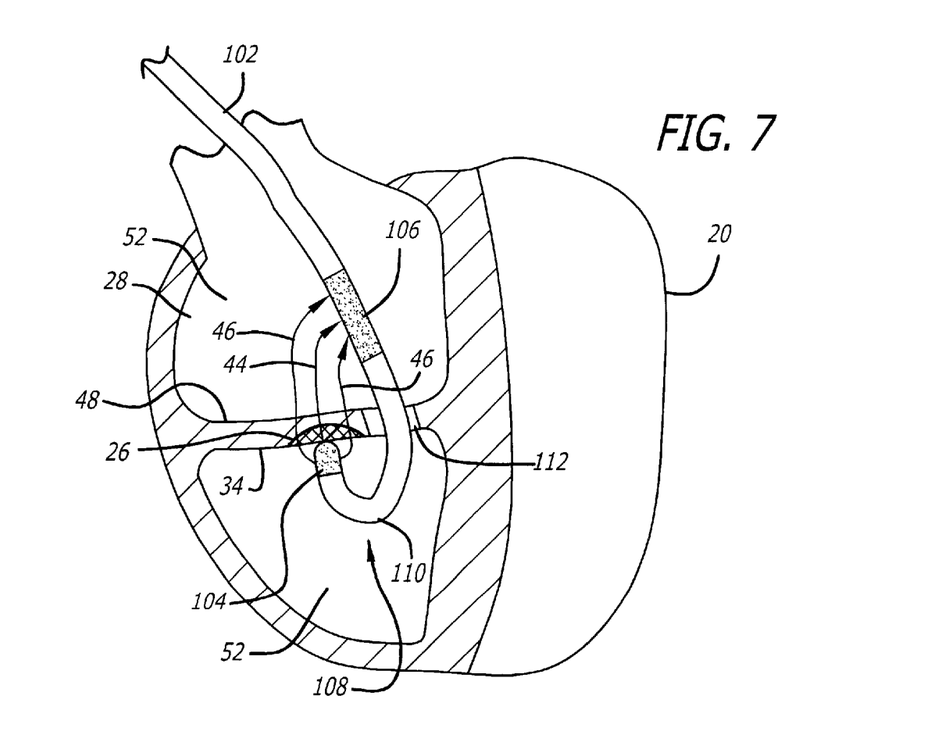
FIG. 7 is a cross section depicting a catheter with an ablation electrode disposed against a surface of a cavity within a biological site and a return electrode within another cavity of the biological site.

Referring to FIGS. 6 and 7, another embodiment of the invention includes a single catheter 102 that includes one or more ablation electrodes 104 or primary electrodes and one or more secondary electrodes 106. If more than one secondary electrode 106 is used, each secondary electrode is connected to the switching device 84 (FIG. 3) to selectively couple one of the secondary electrodes to the electrical device 85 (FIG. 3). In FIG. 6 the distal segment 108 of the catheter 102 is depicted as being bent or steered in a "J-shape" 110 around a portion of the biological site 20 with the primary electrode 104 adjacent one side of the target tissue region 34 and the secondary electrode 106 adjacent the opposite side of the target tissue region. In this embodiment, the tissue current 44 enters the tissue 34 directly from the primary electrode 104, passes through the lesion volume 26 in the direction of the secondary electrode 106, exits the opposite surface 48 of the tissue and enters the secondary electrode 106 without traversing other parts of the biological body 22 (FIG. 3). The blood current 46 first enters the blood 52 surrounding the ablation electrode 104, then enters the tissue 34, exits the opposite surface 48 of the tissue and enters the secondary electrode 106. This embodiment is beneficial in that it permits the advantage of having the target tissue region 34 located between the primary electrode 104 and the secondary electrode 106 while utilizing fewer instruments and not conducting the current 44, 46 through other tissues.

In FIG. 7 the distal segment 108 of the catheter 102 is depicted passing through an orifice 112 within the biological site 20 and being bent or steered in a "J-shape" 110 so that a tip primary electrode 104 on the catheter is adjacent the target tissue region 34 and the secondary electrode 106 is positioned within a cavity 28 in the biological site on the opposite side of the target tissue region 34. In this embodiment, the tissue current 44 enters the target tissue 34 directly from the primary electrode 104, passes through the lesion volume 26 in the direction of the secondary electrode 106, exits the opposite surface 48 of the tissue 34, passes through a blood pool 52 and enters the secondary electrode 106 without traversing other parts of the biological body 22. The blood current 46 first enters the blood 52 surrounding the primary electrode 104, then enters the tissue 34, exits the opposite surface 48 of the tissue, passes through the blood pool 52 and enters the secondary electrode 106.

Although not shown, the single catheter 102 having one or more ablation electrodes 104 or primary electrodes and one or more secondary electrodes 106, as disclosed in the discussion regarding FIGS. 6 and 7, can be used in conjunction with the backplates 36 of the earlier discussed secondary electrode system 62 (FIG. 3) so that the operator or controller 66 can select a secondary electrode from either the backplates 36 or the secondary electrodes 106 on the catheter 102. As with the catheter based secondary electrode system 86 of FIG. 4, this embodiment enables the operator to further limit the area in which the energy will travel within the biological body 22.

Referring again to FIGS. 1, 2 and 3, the ablation system 56 can alternatively be used with a backplate 36 that is not in the optimal position (FIGS. 1 and 2) in order to create a lesion 26 with a shallower depth such as shown in FIG. 1, or to reduce collateral damage to other biological tissue that lies within the current path between the backplate 36 or secondary electrode and the ablation electrode 30 or primary electrode when the backplate is in the optimal position. By selecting a different backplate 36 that is not in the optimal position, the target tissue region 34 is no longer positioned between the primary electrode 30 and the secondary electrode 36, and the current is, therefore, no longer concentrated toward the target tissue region 34.

Figure 8:
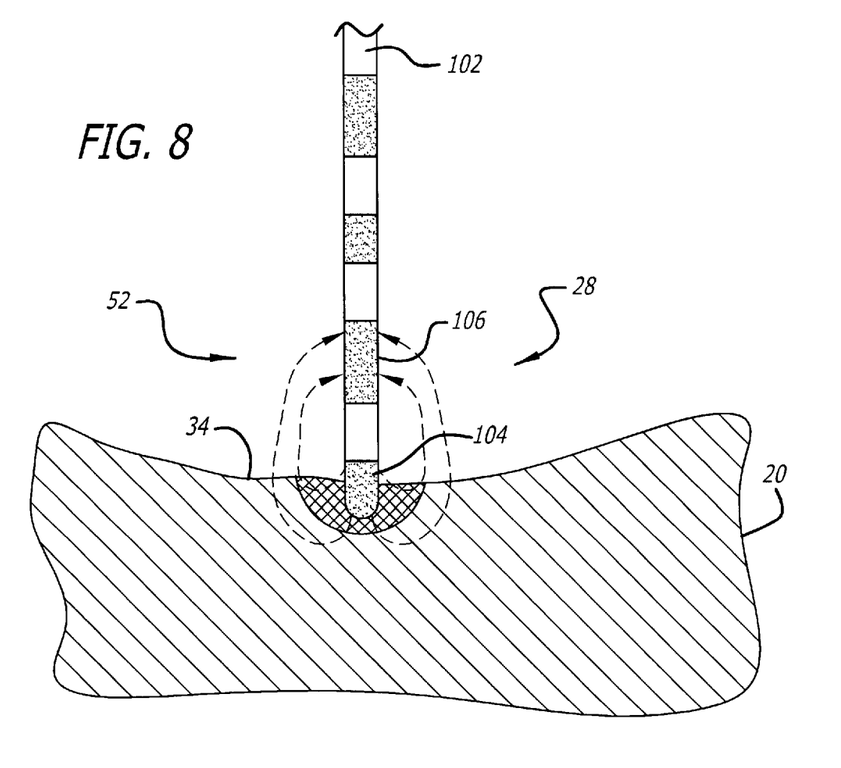
FIG. 8 depicts a catheter with an ablation electrode against a surface of a biological site and a return electrode located proximal the biological site.
Figure 9:
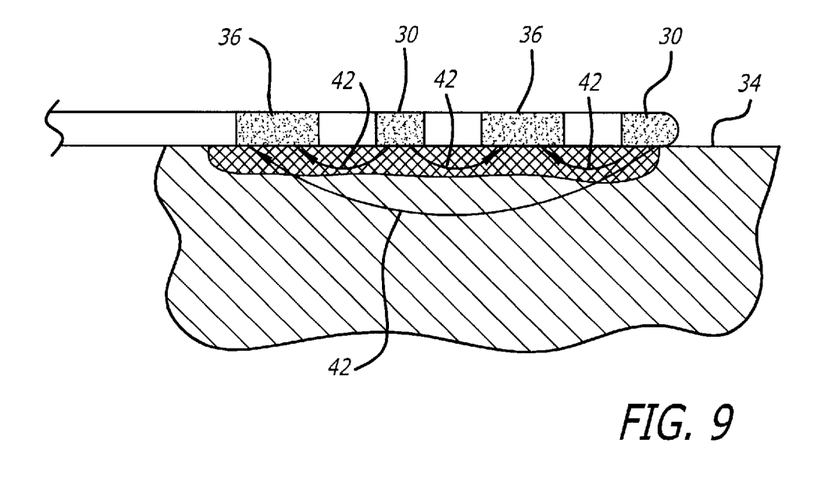
FIG. 9 depicts a catheter with multiple ablation electrodes and return electrodes positioned adjacent a biological site.

With reference to FIG. 8, the single catheter 102 described in FIGS. 6 and 7 may also be used to create a lesion with a shallower depth and to reduce collateral damage to surrounding biological tissue. For instance, the tip primary electrode 104 can be placed in a head on direction against the target tissue region 34 within a cavity 28 of a biological site 20 while the secondary electrode 106 is positioned behind the tip primary electrode 30 in a blood pool 52 within the cavity. This configuration is similar to the non-optimal backplate 36 position (FIGS. 1, 2 and 3) discussed above wherein the current that enters the tissue 34 conducts toward the blood 52 and away from the biological tissue, thereby causing more energy to be dissipated into the blood. Alternatively, as depicted in FIG. 9, the single catheter 102 of FIGS. 6 and 7 can be laid against the target tissue region 34 to create a shallow lesion. In this configuration, two primary electrodes 30 and two secondary electrodes 36 are alternately arranged and the electrodes 30, 36 are depicted adjacent the target tissue region 34. The current 42 can be selectively directed and/or switched between either of the primary electrodes 30 and either of the secondary electrodes 36 to form the desired lesion.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A system for delivering energy to any one of a plurality of tissue regions at a biological site within a biological body, said system comprising:

at least one primary electrode adapted to be positioned adjacent tiny one of the plurality of tissue regions;

a plurality of secondary electrodes adapted to be positioned about the biological site such that any one of the plurality of tissue regions is interposed between at least one of the secondary electrodes and the at least one primary electrode;

a power generator adapted to provide power to the at least one primary electrode;

a switching device adapted to couple anyone of the secondary electrodes to an electrical device, the electrical device adapted to maintain the coupled secondary electrode at a voltage level different from the primary electrode such that current flows from the primary electrode through the tissue region to the coupled secondary electrode; and a controller programmed to, based upon an electrical-based measurement between the secondary electrodes and the at least one primary electrode, select one of the secondary electrodes for coupling with the electrical device and to command the switching device to couple the selected secondary electrode to the electrical device.

2. The system of claim 1 wherein the at least one primary electrode is disposed at a distal segment of a first catheter adapted to be positioned within the biological body.

3. The system of claim 1 wherein at least one of the secondary electrodes comprises a backplane adapted to be positioned adjacent the exterior of the biological body.

4. The system of claim 1 wherein at least one of the secondary electrodes is disposed at a distal segment oh second catheter adapted to be positioned within the biological body.

5. The system of claim 1 wherein the at least one primary electrode and at least one of the secondary electrodes are disposed at a distal segment of a catheter adapted to be positioned within the biological body.

6. The system of claim 1 wherein the controller is programmed to measure the impedance between each of the secondary electrodes and the primary electrode, compare the impedances and based on the comparison, select the secondary electrode for coupling to the electrical device.

7. The system of claim 6 wherein to measure impedance between each of the secondary electrodes and the primary electrode, the controller is programmed to:

apply an electric pulse at the primary electrode;

sense the electric pulse at a first of the secondary electrodes;

calculate the difference between the voltage of the pulse signal and the voltage of the sensed signal to determine the impedance; and repeat the process for each of the remaining secondary electrodes.

8. The system of claim 1 wherein the controller is programmed to measure the conduction time of an electric pulse between each of the secondary electrodes and the primary electrode, compare the conduction times and based on the comparison, select the secondary electrode for coupling to the electrical device.

9. The system of claim 8 wherein to measure conduction time between each of the secondary electrodes and die primary electrode, the controller is programmed to:

apply an electric pulse at the primary electrode;

sense the electric pulse at a first of the secondary electrodes;

calculate the time it takes for the pulse to conduct from the primary electrode to the secondary electrode to determine the conduction time; and repeal the process for each of the remaining secondary electrodes.

10. A system for providing a plurality of selectable current paths through a plurality of tissue regions within a biological site within a biological body, said system comprising:

at least one primary electrode adapted to be positioned adjacent any one of the plurality of tissue regions and to serve as a first electrical pole;

a plurality of secondary electrodes adapted to be positioned about the biological site such that any one of the plurality of tissue regions is interposed between at least one of the secondary electrodes and the at least one primary electrode, each of the secondary electrodes adapted to be selected to serve as a second electrical pole having a voltage different then the first electrical pole such that current flows through the tissue region between the first and second electrical poles; and a selection system programmed to select one of the secondary electrodes as the second electrical pole, the selection system including a switching device adapted to couple anyone of the secondary electrodes to an electrical device, the electrical device adapted to maintain the selected coupled secondary electrode at a voltage level different than the primary electrode, and a controller programmed to, based upon an electrical-based measurement between the secondary electrodes and the at least one primary electrode, select one of the secondary electrodes for coupling with the electrical device and to command the switching device to couple the selected secondary electrode to the electrical device.

11. The system of claim 10 wherein the controller is programmed to measure the impedance between each of the secondary electrodes and the primary electrode, compare the impedances and based on the comparison, select the secondary electrode for coupling to the electrical device.

12. The system of claim 11 wherein to measure impedance between each of the secondary electrodes and the primary electrode, the controller is programmed to:

apply an electric pulse at the primary electrode;

sense the electric pulse at a first of the secondary electrodes;

calculate the difference between the voltage of the pulse signal and the voltage of the sensed signal to determine the impedance; and repeat the process for each of the remaining secondary electrodes.

13. The system of claim 10 wherein the controller is programmed to measure the conduction time of an electric pulse between each of the secondary electrodes and the primary electrode, compare the conduction times and based on the comparison, select the secondary electrode for coupling to the electrical device.

14. The system of claim 13 wherein to measure conduction time between each of the secondary electrodes and the primary electrode, the controller is programmed to:

apply an electric pulse at the primary electrode;

sense the electric pulse at a first of the secondary electrodes;

calculate the time it takes for the pulse to conduct from the primary electrode to the secondary electrode to determine the conduction time; and repeat the process for each of the remaining secondary electrodes.

15. The system of claim 10 wherein the at least one primary electrode is disposed at a distal segment of a first catheter adapted to be positioned within the biological body.

16. The system of claim 10 wherein at least one of the secondary electrodes comprises a backplate adapted to be positioned adjacent the exterior of the biological body.

17. The system of claim 10 wherein at least one of the secondary electrodes is disposed at a distal segment of a second catheter adapted to be positioned within the biological body.

18. The system of claim 10 wherein the at least one primary electrode and at least one of the secondary electrodes are disposed at a distal segment of a catheter adapted to be positioned within the biological body.

19. A method for selectively ablating any one of a plurality of tissue regions within a biological site of a biological body, said method comprising:

positioning at least one primary electrode adjacent one of the plurality of tissue regions;

positioning a plurality of secondary electrodes about the biological site;

providing a switching device adapted to couple anyone of the secondary electrodes to an electrical device;

providing a controller programmed to select one of the secondary electrodes for coupling with the electrical device, based upon an electrical-based measurement between the secondary electrodes and the at least one primary electrode;

selecting which of the plurality of secondary electrodes is positioned, based upon the electrical-based measurement, such that the tissue region adjacent the at least One primary electrode is interposed between the primary electrode and the secondary electrode;

coupling the selected secondary electrode to the electrical device via the switching device;

providing energy to the primary electrode; and maintaining the selected secondary electrode at a voltage level different from the primary electrode such that current flows from the primary electrode through the tissue region to the selected secondary electrode.

20. The method of claim 19 wherein positioning the plurality of secondary electrodes about the biological site comprises positioning at least one secondary electrode adjacent the biological body at each of the anterior, posterior, lateral, and septal positions on the biological body.

21. The method of claim 19 wherein positioning the plurality of secondary electrodes about the biological site comprises positioning the secondary electrodes adjacent the biological body in several locations about the outer surface of the biological body.

22. The method of claim 19 wherein positioning the plurality of secondary electrodes about the biological site comprises positioning at least one of the secondary electrodes within the biological body and about the biological site such that the tissue region is interposed between the primary electrode and the secondary electrode.

23. The method of claim 19 wherein positioning the plurality of secondary electrodes about the biological site comprises positioning a plurality of secondary electrodes within the biological body and about the biological site.

24. A method for selectively ablating any one of a plurality of tissue regions within a biological site of a biological body, said method comprising:

positioning at least one primary electrode adjacent one of the plurality of tissue regions;

positioning a plurality of secondary electrodes about the biological site;

selecting which of the plurality of secondary electrodes is positioned such that the tissue region adjacent the at least one primary electrode is interposed between the primary electrode and the secondary electrode, said selecting including,     measuring the time it takes for a pulse to conduct from the primary electrode to each of the secondary electrodes,     comparing the conduction times, and     selecting the secondary electrode with the shortest conduction time;

providing energy to the primary electrode; and maintaining the selected secondary electrode at a voltage level different from the primary electrode such that current flows from the primary electrode through the tissue region to the selected secondary electrode.

25. The method of claim 24 wherein measuring the conduction time between each of the secondary electrodes and the primary electrode comprises:

a) applying an electric pulse at the primary electrode;

b) sensing the electric pulse at a first of the secondary electrodes;

c) calculating the time it takes for the pulse to conduct from the primary electrode to the secondary electrode to determine the conduction time; and d) repeating a, b and c for each of the remaining secondary electrodes.

26. A system for delivering energy to any one of a plurality of tissue regions at a biological site within a biological body, said system comprising:

at least one primary electrode adapted to be positioned adjacent any one of the plurality of tissue regions;

a plurality of secondary electrodes adapted to be positioned about the biological site such that any one of the plurality of tissue regions is interposed between at least one of the secondary electrodes and the at least one primary electrode;

a power generator adapted to provide power to the at least one primary electrode; and a switching device adapted to selectively couple one of the secondary electrodes to an electrical device via a mechanical switch, the electrical device adapted to maintain the selected secondary electrode at a voltage level different from the primary electrode such that current flows from the primary electrode through the tissue region to the selected secondary electrode.

27. A method for selectively ablating any one of a plurality of tissue regions within a biological site of a biological body, said method comprising:

positioning at least one primary electrode adjacent one of the plurality of tissue regions;

positioning a plurality of secondary electrodes about the biological site;

selecting which of the plurality of secondary electrodes is positioned such that the tissue region adjacent the at least one primary electrode is interposed between the primary electrode and the secondary electrode, said selecting including,     measuring the impedance between each of the secondary electrodes and the primary electrode, including,     a) applying an electric pulse at the primary electrode,     b) sensing the electric pulse at a first of the secondary electrodes,     c) calculating the difference between the voltage of the pulse signal and the voltage of the sensed signal to determine the impedance, and     d) repeating a, b and c for each of the remaining secondary electrodes,     comparing the impedance between each of the secondary electrodes and the primary electrode, and     selecting the secondary electrode with the lowest impedance;

providing energy to the primary electrode; and maintaining the selected secondary electrode at a voltage level different from the primary electrode such that current flows from the primary electrode through the tissue region to the selected secondary electrode.

\* \* \* \* \*

UNITED STATES PATENT AND TRADEMARK OFFICE
CERTIFICATE OF CORRECTION

PATENT NO. : 6,740,080 B2
DATED : May 25, 2004
INVENTOR(S) : Mudit K. Jain, Milton M. Morris and Bruce KenKnight It is certified that error appears in the above-identified patent and that said Letters Patent is hereby corrected as shown below:

Column 12,
Line 6, delete "tiny" and insert -- any --.
Line 36, delete "oh" and insert -- of --.
Line 66, delete "die" and insert -- the --.

Column 14,
Line 36, delete "One" and insert -- one --.

Signed and Sealed this

Fourth Day of January, 2005

JON W. DUDAS
*Director of the United States Patent and Trademark Office*